(12) United States Patent
Schramm et al.

(10) Patent No.: US 9,107,840 B2
(45) Date of Patent: Aug. 18, 2015

(54) HORMONAL CONTRACEPTIVE CONTAINING A COMBINATION OF ETHINYLOESTRADIOL AND CHLORMADINONE ACETATE

(75) Inventors: Georg Schramm, Stolberg (DE); Rainer Henske, Essen (DE)

(73) Assignee: Richter Gedeon Nyrt., Budapest (HU)

( * ) Notice: Subject to any disclaimer, the term of this patent is extended or adjusted under 35 U.S.C. 154(b) by 2596 days.

(21) Appl. No.: 11/009,362

(22) Filed: Dec. 10, 2004

(65) Prior Publication Data

US 2005/0267082 A1 Dec. 1, 2005

(30) Foreign Application Priority Data

May 28, 2004 (DE) .......................... 10 2004 026 679

(51) Int. Cl.
  *A61K 31/56* (2006.01)
  *A61K 9/28* (2006.01)
  *A61K 31/565* (2006.01)
  *A61K 31/57* (2006.01)

(52) U.S. Cl.
  CPC ............. *A61K 9/2866* (2013.01); *A61K 31/565* (2013.01); *A61K 31/57* (2013.01)

(58) Field of Classification Search
  USPC ........................................................ 514/170
  See application file for complete search history.

(56) References Cited

U.S. PATENT DOCUMENTS

| | | | |
|---|---|---|---|
| 6,190,693 B1 | 2/2001 | Kafrissen et al. | |
| 6,265,393 B1 | 7/2001 | Heinrichs | 514/178 |
| 6,312,722 B1 | 11/2001 | Schmidt-Gollwitzer et al. | |
| 6,451,779 B1 | 9/2002 | Hesch | 514/171 |
| 6,500,814 B1 | 12/2002 | Hesch | |
| 6,511,970 B1 | 1/2003 | Rodriguez | |
| 2002/0061875 A1 | 5/2002 | Gast | |
| 2004/0063721 A1 | 4/2004 | Deecher | |
| 2004/0219174 A1* | 11/2004 | Kulmann | 424/400 |

FOREIGN PATENT DOCUMENTS

| | | |
|---|---|---|
| DE | 43 21 957 A1 | 1/1995 |
| DE | 43 21 957 C2 | 9/1995 |
| DE | 34 86 442 T2 | 6/1997 |
| DE | 197 05 229 C2 | 4/1999 |
| DE | 197 39 916 C2 | 9/2001 |
| DE | 698 04 918 T2 | 11/2002 |
| EP | 0 253 607 A1 | 1/1988 |
| EP | 0 398 460 B1 | 5/1990 |
| EP | 0 398 460 A2 | 11/1990 |
| EP | 0 398 460 A3 | 11/1990 |
| WO | WO 99/53910 | 10/1999 |
| WO | WO 02/22110 * | 3/2002 |
| WO | WO 2004/098517 A2 | 11/2004 |

OTHER PUBLICATIONS

Vercellini et al., Fertility and Sterility, 2003; 80(3): 560-563.*
"Progestogens With Antiandrogenic Properties", Daniel Raudrant, et al., Drugs 2003, 63 (5), 463-492.
"A Comparative Study of the Hemostatic Effects of Two Monophasic Oral Contraceptives Containing 30 μg Ethinylestradiol and Either 2 MG Chlormadinone Acetate or 150 μg Desogestrel", U.H. Winkler, et al., The European Journal of Contraception and Reproductive Health Care 1999; 4: 145-154.
"Effect of 21-day and 24-day oral contraceptive regimens containing gestodene (60 μg) and ethinyl estradiol (15 μg) on ovarian activity", Helen Sullivan et al., Fertility and Sterility, vol. 72, No. 1, Jul. 1999, 115-120.
"The safety and contraceptive efficacy of a 24-day low-dose oral contraceptive regimen containing gestodene 60 μg and ethinylestradiol 15 μg", Gestodene Study Group 322, The European Journal of Contraception and Reproductive Health Care, 1999, (Suppl. 2): 9-15.
"Orale Kontrazeptiva—Folge 1: Typen and Indikationen", B. Wetzka, et al., MMW-Fortschr. Med. 2001, pp. 40-42.
Non Final Office Action issued on Mar. 12, 2009 by Examiner for corresponding pending U.S. Appl. No. 11/009,361.
Non Final Office Action issued on Apr. 16, 2009 by Examiner for corresponding pending U.S. Appl. No. 11/348,545.
Non Final Office Action issued on Jul. 8, 2008 by Examiner for corresponding pending U.S. Appl. No. 11/009,938.
Non Final Office Action issued on Sep. 3, 2009 by Examiner for corresponding pending U.S. Appl. No. 11/009,938.
Final Office Action issued on Mar. 23, 2009 by Examiner for corresponding pending U.S. Appl. No. 11/009,938.
G. Schramm, Contraceptive Efficacy and Tolerability of Chlormadinone Acetate 2mg/Ethinylestradiol 0.03mg (Belara®), Clinical Drug Invest 2002:22 (4) pp. 221-231.

* cited by examiner

*Primary Examiner* — San-Ming Hui
(74) *Attorney, Agent, or Firm* — Jason D. Voight

(57) ABSTRACT

The present invention relates to a hormonal contraceptive including at least 120 hormone-containing daily units, which contain 5 to 50 μg of ethinyloestradiol and 1 to 5 mg of chlormadinone acetate, and optionally 7 to 3 hormone-free daily units for uninterrupted oral administration to women.

5 Claims, No Drawings

HORMONAL CONTRACEPTIVE CONTAINING A COMBINATION OF ETHINYLOESTRADIOL AND CHLORMADINONE ACETATE

CROSS-REFERENCE OF RELATED APPLICATIONS

This application claims priority from German Patent Application No. 10 2004 026 679.4 filed on May 28, 2004.

BACKGROUND OF THE INVENTION

1. Field of the Invention

The present invention relates to a hormonal contraceptive for the oral, uninterrupted administration of at least 120 hormone-containing daily units, which contain 5 to 50 µg of ethinyloestradiol and 1 to 5 mg of chlormadinone acetate, and optionally 7 to 3 hormone-free daily units.

Women are increasingly demanding that hormonal contraceptives suppress as much bleeding, such as withdrawal bleeding or intermenstrual bleeding, as possible since the suppression of bleeding results in fewer menstrual complaints, better hygiene, a better quality of life and lower levels of blood loss or iron deficiency.

2. Brief Description of Related Developments

A low dosage, oral contraceptive comprising monophasic administration of a combination of oestrogen and progestin over 60 to 110 successive days, followed by a 3 to 7 day interval in taking is already known from DE 698 04 918, wherein the daily quantity of oestrogen or gestagen is equivalent to 5 to 35 µg of ethinyloestradiol or 0.025 to 10 mg of norethisterone acetate.

There still remains a further requirement to bring about a greater reduction in the number of instances of bleeding, such as withdrawal bleeding or/or intermenstrual bleeding, in order to achieve an improvement in quality of life for women and, inter alia, to provide ongoing treatment of androgen-dependent complaints or conditions.

SUMMARY OF THE INVENTION

It was accordingly an object of the present invention to provide a hormonal contraceptive which, in comparison with the prior art, permits a substantial reduction in the number of instances of bleeding, in particular of withdrawal bleeding and/or intermenstrual bleeding.

This object is achieved by the provision of the hormonal contraceptive according to the invention for uninterrupted, oral administration to women, which contraceptive is characterised in that it comprises of at least 120 hormone-containing daily units, which contain 5 to 50 µg of ethinyloestradiol and 1 to 5 mg of chlormadinone acetate, and optionally of 7 to 3 hormone-free daily units.

In one embodiment according to the invention, the hormonal contraceptive may provide hormone-containing daily units for uninterrupted administration for a period of 120 days up to several years, preferably up to 2 years, particularly preferably up to 1 year, optionally followed by 7 to 3 hormone-free daily units.

The monophasic taking regimen of the long-term hormonal contraceptive according to the invention not only ensures reliable hormonal contraception, but also a considerable reduction in the instances of bleeding, in particular of withdrawal bleeding and/or intermenstrual bleeding, relative to the prior art.

Taking of the hormonal contraceptive without interruption may furthermore be carried out for therapeutic reasons, such as for example for the treatment of bleeding disorders, dysmenorrhoea, cycle-dependent gynaecological conditions, such as endometriosis, polycystic ovarian syndrome (PCOS), uterus myomatosus, functional cysts and/or in conditions dependent on the menstrual cycle, such as premenstrual syndrome, in particular headache/migraine, conditions influenced by the menstrual cycle, such as epilepsy, multiple sclerosis, diabetes mellitus, depression, schizophrenia, asthma, Parkinson's disease and/or for the treatment of androgenically induced disorders, such as seborrhoea, acne, alopecia or hirsutism.

Taking the hormonal contraceptive according to the invention may furthermore alleviate typical symptoms in the pre- and perimenopause. The hormonal contraceptive according to the invention is accordingly in particular especially suitable for women over 35 years old, i.e. pre- and perimenopausal women.

Typical symptoms in the pre- and perimenopause are, for example, an irregular menstrual cycle, vasomotor disorders, such as hot flushes, sweating and/or insomnia. Moreover many women in the pre- and perimenopause also suffer from the above-listed androgen-dependent symptoms. In particular in those over 35 years of age, the hormonal fluctuations may result in unwanted facial hair, a lower voice, skin disorders and/or hair loss.

Taking the hormonal contraceptive according to the invention for at least 120 days may, inter alia, at least alleviate the androgen-dependent symptoms in the pre- and perimenopause.

The present invention accordingly also provides the use of a combination of ethinyloestradiol and chlormadinone acetate for the production of a contraceptive for the monophasic, uninterrupted administration of hormone-containing daily units to women for a duration of at least 120 days, preferably of 120 days to several years, particularly preferably for up to 2 years, very particularly preferably for up to 1 year and optionally 3 to 7 successive, hormone-free daily units and/or for the treatment of at least one of the complaints or diseases comprising androgen-dependent symptoms, such as hirsutism, androgenetic alopecia, acne, seborrhoea and/or bleeding disorders, dysmenorrhoea and/or gynaecological disorders dependent on the menstrual cycle, such as endometriosis, PCOS, uterus myomatosus, functional cysts and/or cycle-dependent conditions, such as premenstrual syndrome, in particular headaches/migraine, and/or conditions influenced by the menstrual cycle, such as epilepsy, multiple sclerosis, diabetes mellitus, depression, schizophrenia, asthma, Parkinson's disease.

The hormonal contraceptive according to the invention contains ethinyloestradiol as the oestrogen and chlormadinone acetate as the gestagen. By taking this combination of ethinyloestradiol and chlormadinone acetate over at least 120 days, the contraceptive according to the invention not only ensures reliable contraception, but also a considerable reduction in the instances of bleeding, in particular of withdrawal bleeding and/or intermenstrual bleeding, relative to the prior art and improved wellbeing.

Therapeutic treatment of the above-listed conditions or diseases is moreover also possible.

Each hormonal daily unit of the hormonal contraceptive or pharmaceutical preparation according to the invention preferably contains 1 to 5 mg of chlormadinone acetate and 5 to 50 µg of ethinyloestradiol, preferably 1 to 3 mg of chlormadinone acetate and 15 to 30 µg of ethinyloestradiol, particularly preferably 1 to 2 mg of chlormadinone acetate and 20 to 30 µg of ethinyloestradiol.

According to one embodiment according to the invention, the contraceptive according to the invention may contain 15 µg, 20 µg or 30 µg of ethinyloestradiol and 1 mg, 2 mg, 3 mg, 4 mg or 5 mg of chlormadinone acetate.

All the hormone-containing daily units of the monophasic contraceptive according to the invention preferably each contain the same quantity of chlormadinone acetate or ethinyloestradiol.

Taking the contraceptive according to the invention for a period of at least 120 days up to several years reduces the number of instances of bleeding, such as withdrawal bleeding and/or intermenstrual bleeding, if the daily units preferably contain from 1 to 5 mg of chlormadinone acetate and from 5 to 50 µg of ethinyloestradiol.

Taking the hormone-containing daily units without interruption over a period of at least 120 days up to several years, preferably of up to 2 years, very particularly preferably of up to one year may be followed by an interval in taking of 7 to 3 days or by taking 7 to 3 hormone-free daily units, before taking of a further hormonal contraceptive according to the invention is begun.

The present invention accordingly also provides a kit comprising a plurality of the contraceptives according to the invention in each case for the uninterrupted administration of at least 120 hormone-containing daily units, which each contain 5 to 50 µg of ethinyloestradiol and 1 to 5 mg of chlormadinone acetate, and optionally 7 to 3 hormone-free daily units, wherein the uninterrupted administration of the next contraceptive from the kit immediately follows on from the administration of the hormone-free daily units or from an interval in taking of a corresponding length.

The daily units of the hormonal contraceptive according to the invention may preferably assume the form of tablets. Production methods for such daily units are known to the person skilled in the art. Known auxiliary substances may optionally also be used as additives in addition to the combination of chlormadinone acetate and ethinyloestradiol.

EXAMPLES

Example 1

| Composition | Per tablet |
| --- | --- |
| Ethinyloestradiol | 0.020 mg |
| Chlormadinone acetate | 2.000 mg |
| Povidone K30 | 3.000 mg |
| Lactose | 31.980 mg |
| Maize starch | 12.000 mg |
| Magnesium stearate | 0.500 mg |
| Highly disperse silicon dioxide | 0.500 mg |

Ethinyloestradiol (EE) and povidone K30 (polyvinylpyrrolidone) were dissolved in 600 ml of ethanol. Chlormadinone acetate (particle size 90%<50 µm), lactose and maize starch were mixed in a mixer/pelletiser (Diosna P25) for 5 mins and then moistened thoroughly and mixed with the ethanolic EE/PVP solution. The moist composition was forced through a 3 mm screen and dried in a vacuum drying cabinet. The dried granular product was disagglomerated through a 0.6 mm screen, mixed with magnesium stearate and highly disperse silicon dioxide and pressed on a tablet press with 5 mm punches into tablets with a weight of 50 mg.

The tablets were coated with a methylhydroxypropylcellulose-based coating (e.g. Opadry YS-1-2184 made by Colorcon); coating composition 2 mg per tablet, dosage form of the contraceptive comprising 120 daily units.

Example 2

| Composition | Per tablet |
| --- | --- |
| Ethinyloestradiol | 0.03 mg |
| Chlormadinone acetate | 2.000 mg |
| Povidone K30 | 3.000 mg |
| Lactose | 31.970 mg |
| Maize starch | 12.000 mg |
| Magnesium stearate | 0.500 mg |
| Highly disperse silicon dioxide | 0.500 mg |

Ethinyloestradiol (EE) and povidone K30 (PVP) were dissolved in 600 ml of ethanol. Chlormadinone acetate (particle size 90%<50 µm), lactose and maize starch were mixed in a mixer/pelletiser (Diosna P25) for 5 mins and then moistened thoroughly and mixed with the ethanolic EE/PVP solution. The moist composition was forced through a 3 mm screen and dried in a vacuum drying cabinet. The dried granular product was disagglomerated through a 0.6 mm screen, mixed with magnesium stearate and highly disperse silicon dioxide and pressed on a tablet press with 5 mm punches into tablets with a weight of 50 mg.

The tablets were coated with a methylhydroxypropylcellulose-based coating of the following composition (coating composition 2 mg per tablet)

| Methylhydroxypropylcellulose 6 mPa · s, | 0.1351 kg |
| --- | --- |
| Polyethylene glycol 6000 | 0.0395 kg |
| Propylene glycol | 0.0054 kg |
| Purified water | 1.6200 kg |
| Dosage form comprising 189 daily units | |

In the case of a kit comprising a plurality of dosage forms, there was a 4 day interval in taking between two administration cycles each comprising 189 daily units.

Example 3

| Composition | Per tablet |
| --- | --- |
| Ethinyloestradiol | 0.015 mg |
| Chlormadinone acetate | 2.000 mg |
| Povidone K30 | 4.000 mg |
| Lactose | 63.485 mg |
| Maize starch | 10.000 mg |
| Magnesium stearate | 0.500 mg |

Ethinyloestradiol (EE) and povidone K30 (PVP) were dissolved in 950 ml of ethanol. Chlormadinone acetate (particle size 90%<50 µm), lactose and maize starch were mixed in a mixer/pelletiser (Diosna P25) for 5 mins and then moistened thoroughly and mixed with the ethanolic EE/PVP solution. The moist composition was forced through a 3 mm screen and dried in a vacuum drying cabinet. The dried granular product was disagglomerated through a 0.6 mm screen, mixed with magnesium stearate and pressed on a tablet press with 6 mm punches into tablets with a weight of 80 mg.

The tablets were coated with a methylhydroxypropylcellulose-based coating of the following composition (coating composition 2 mg per tablet)

| | |
|---|---|
| Methylhydroxypropylcellulose 6 mPa · s, | 0.1351 kg |
| Polyethylene glycol 6000 | 0.0395 kg |
| Propylene glycol | 0.0054 kg |
| Purified water | 1.6200 kg |

Dosage form comprising 365 daily units; where the kit comprises more than one of these dosage forms, an interval in taking of 7 days was allowed between 2 tablet-taking cycles.

Example 4

| Composition | Per tablet |
|---|---|
| Ethinyloestradiol | 0.030 mg |
| Chlormadinone acetate | 5.000 mg |
| Povidone K30 | 4.500 mg |
| Lactose | 60.470 mg |
| Maize starch | 10.000 mg |
| Magnesium stearate | 0.500 mg |

Ethinyloestradiol (EE) and povidone K30 (PVP) were dissolved in 950 ml of ethanol. Chlormadinone acetate (particle size 90%<50 µm), lactose and maize starch were mixed in a mixer/pelletiser (Diosna P25) for 5 mins and then moistened thoroughly and mixed with the ethanolic EE/PVP solution. The moist composition was forced through a 3 mm screen and dried in a vacuum drying cabinet. The dried granular product was disagglomerated through a 0.6 mm screen, mixed with magnesium stearate and pressed on a tablet press with 6 mm punches into tablets with a weight of 80 mg.

The tablets were coated with a methylhydroxypropylcellulose-based coating of the following composition (coating composition 1 mg per tablet)

| | |
|---|---|
| Methylhydroxypropylcellulose 6 mPa · s, | 0.068 kg |
| Polyethylene glycol 6000 | 0.020 kg |
| Propylene glycol | 0.002 kg |
| Purified water | 0.810 kg |

A dosage form with 150 daily units for uninterrupted administration; where the kit comprises a plurality of dosage forms or contraceptives according to the invention, there was an interval in taking of 4 days between 2 tablet-taking cycles.

The invention claimed is:

1. A method for the treatment of at least one of androgen-dependent symptoms, bleeding disorders, dysmenorrhoea, conditions dependent on the menstrual cycle, conditions influenced by the menstrual cycle, and premenstrual syndrome, said method comprising administering to a premenopausal or perimenopausal woman daily units comprising a combination of ethinyloestradiol and chlormadinone acetate uninterruptedly for a duration of more than 150 days to up to 2 years, and optionally administering hormone-free daily units to said woman for a subsequent 3 to 7 days.

2. The method according to claim 1, wherein the combination is administered for at least 1 year.

3. The method according to claim 1, wherein the combination comprises about 5 to 50 µg of ethinyloestradiol and about 1 to 5 mg of chlormadinone acetate.

4. The method according to claim 1, wherein each of the daily units comprises the same quantity of ethinyloestradiol.

5. The method according to claim 1, wherein each of the daily units comprises the same quantity of chlormadinone acetate.

\* \* \* \* \*